United States Patent
Elenbaas et al.

(10) Patent No.: US 10,760,130 B2
(45) Date of Patent: Sep. 1, 2020

(54) PREDICTIVE BIOMARKER FOR HYPOXIA-ACTIVATED PRODRUG THERAPY

(71) Applicant: MOLECULAR TEMPLATES, INC., Austin, TX (US)

(72) Inventors: Brian A. Elenbaas, Melrose, MA (US); Antonio Gualberto, Acton, MA (US); Charles Praray Hart, Mountain View, CA (US)

(73) Assignee: MOLECULAR TEMPLATES, INC., Austin, TX (US)

( * ) Notice: Subject to any disclaimer, the term of this patent is extended or adjusted under 35 U.S.C. 154(b) by 160 days.

(21) Appl. No.: 15/528,067

(22) PCT Filed: Nov. 18, 2015

(86) PCT No.: PCT/US2015/061248
§ 371 (c)(1),
(2) Date: May 18, 2017

(87) PCT Pub. No.: WO2016/081547
PCT Pub. Date: May 26, 2016

(65) Prior Publication Data
US 2018/0334716 A1    Nov. 22, 2018

Related U.S. Application Data

(60) Provisional application No. 62/081,768, filed on Nov. 19, 2014.

(51) Int. Cl.
| | |
|---|---|
| *C12Q 1/6883* | (2018.01) |
| *A61K 31/675* | (2006.01) |
| *C07F 9/655* | (2006.01) |
| *C07F 9/6553* | (2006.01) |
| *C07F 9/6506* | (2006.01) |
| *G01N 33/573* | (2006.01) |

(Continued)

(52) U.S. Cl.
CPC .......... *C12Q 1/6883* (2013.01); *A61K 31/675* (2013.01); *A61K 31/7068* (2013.01); *A61K 45/06* (2013.01); *C07F 9/6506* (2013.01); *C07F 9/65515* (2013.01); *C07F 9/655345* (2013.01); *C12Q 1/6886* (2013.01); *G01N 33/5011* (2013.01); *G01N 33/573* (2013.01); *G01N 33/574* (2013.01); *A61K 9/0019* (2013.01); *C12Q 2600/106* (2013.01); *C12Q 2600/158* (2013.01); *G01N 2333/988* (2013.01); *G01N 2800/52* (2013.01); *G01N 2800/7038* (2013.01)

(58) Field of Classification Search
None
See application file for complete search history.

(56) References Cited

U.S. PATENT DOCUMENTS

2011/0182907 A1    7/2011   Leu et al.

FOREIGN PATENT DOCUMENTS

| WO | 2013116385 | * | 8/2013 |
|---|---|---|---|
| WO | WO-2013/116385 A1 | | 8/2013 |

OTHER PUBLICATIONS

Sedoris et al. BMC Cancer 2010, 10:157 (Year: 2010).*

(Continued)

*Primary Examiner* — Karl J Puttlitz
(74) *Attorney, Agent, or Firm* — Foley & Lardner LLP

(57) ABSTRACT

Enolase levels are predictive of the probability that a cancer patient will respond favorably to cancer therapy involving administration of hypoxia-activated achiral phosphoramide mustards.

9 Claims, 6 Drawing Sheets

(51) Int. Cl.
    *C12Q 1/6886* (2018.01)
    *G01N 33/574* (2006.01)
    *A61K 45/06* (2006.01)
    *A61K 31/7068* (2006.01)
    *G01N 33/50* (2006.01)
    *A61K 9/00* (2006.01)

(56) References Cited

OTHER PUBLICATIONS

Song et al. Molecular Cancer 2014, 13:65 (Year: 2014).*
Diaz-Ramos et al., Journal of Biomedicine and Biotechnology, vol. 2012, pp. 1-12 (Year: 2012).*
FEBS Journal 278 (2011) 1064-1074 (Year: 2011).*
Toschi et al., Future Oncology 2005, 1(1), 7-17 (Year: 2005).*
Chemotherapy of Neoplastic Diseases in Goodman & Gilman's Manual of Pharmacology and Therapeutics, McGraw-Hill, 2008 (Year: 2008).*
Capello, M. et al. (2011) "Alpha-enolase: a promising therapeutic and diagnostic tumor target," FEBS Journal 278:1064-1074.
Rubio-Viqueira, B. et al. (2007) "Optimizing the development of targeted agents in pancreatic cancer: tumor fine-needle aspiration biopsy as a platform for novel prospective ex vivo drug sensitivity assays," Mol Cancer Ther. 6(2):515-523.
International Search Report and Written Opinion (ISA/RU) in International Application No. PCT/US2015/061248, dated Mar. 10, 2016.

* cited by examiner

PREDICTIVE BIOMARKER FOR HYPOXIA-ACTIVATED PRODRUG THERAPY

CROSS-REFERENCE TO RELATED APPLICATIONS

This application is a national phase entry under 35 U.S.C. § 371 of International Application No. PCT/US2015/061248, filed Nov. 18, 2015, which claims priority under 35 U.S.C. § 119(e) to U.S. Provisional Patent Application No. 62/081,768, filed Nov. 19, 2014, the content of each of which is incorporated herein by reference in its entirety.

FIELD OF INVENTION

Provided herein are methods related to screening and/or treating cancer patients, based on their enolase level profile, with hypoxia-activated achiral phosphoramide mustards.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment causes adverse side effects in patients and can limit the amount of anticancer drug administered to a cancer patient. It is also difficult to kill cancer cells in hypoxic regions distant from the vasculature where anticancer drugs fail to penetrate.

Many cancer cells are more hypoxic relative to normal cells. Tumor hypoxia is associated with resistance to anti-cancer therapies, cancer relapse, and poor prognosis. Certain drugs in preclinical and clinical development target hypoxic cancer cells. These drugs, called hypoxia-activated prodrugs or "HAPs" are administered in an inactive, or prodrug, form but are activated, and become toxic, in a hypoxic environment. US 2010/0137254 and US 2010/0183742, each of which is incorporated herein by reference, describe HAPs such as those having a structure defined by formula (I), below:

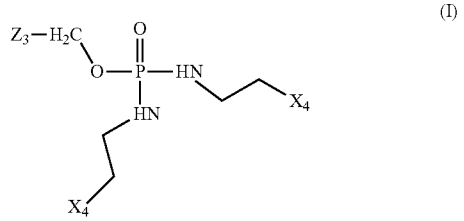

where $Z_3$ is selected from the group consisting of:

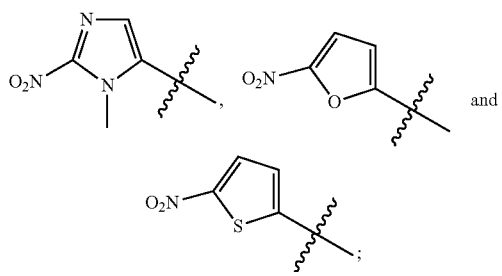

and
$X_4$ is Cl or Br.

The compounds known as TH-302 and TH-281 are particularly promising therapeutic candidates. TH-302 (see Duan et al., 2008, J. Med. Chem. 51: 2412-2420, incorporated herein by reference), known by the chemical name (2-bromoethyl)({[(2-bromoethyl)amino][(2-nitro-3-methyl-imidazol-4-yl)methoxy]phosphoryl})amine, has the structure represented below:

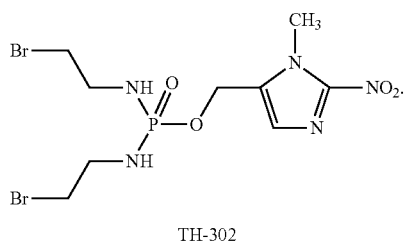 [SMILES: Cn1c(COP(=O)(NCCBr)NCCBr)cnc1[N+](=O)[O-]]

TH-302

Another promising HAP is TH-281, which differs from TH-302 only in that it has 2-chloroethyl groups instead of the 2-bromoethyl groups present in TH-302.

The aforementioned HAPs can be used in combination with other drugs, for the treatment of pancreatic cancer or any other cancer, such as gemcitabine, gemcitabine in combination with nab-paclitaxel (Abraxane), or FOLFIRINOX based on folinic acid (Leucovorin), fluorouracil (5-FU), irinotecan (Camptosar) and oxaliplatin (Eloxatin) (see e.g., WO 2013/126539, PCT/US2014/047885, and Conroy et al., 2013, Current Oncology Reports 15(2): 182-189; each incorporated herein by reference).

However, while nearly all tumors contain hypoxic regions, there is a wide variability among patients in how hypoxic a tumor of a given cancer type may be. For example, using median tumor $pO_2$ (mm Hg) as a measure of tumor hypoxia, one study of 33 soft tissue sarcoma patients showed that the median tumor pO2 ranged from about 1 to about 70 mm Hg (see Nordsmark et al., 2001, Brit. J. Cancer 84(8): 1070-1075). Another study of 58 head and neck cancer patients showed the hypoxic fraction ranged from just above 90% to 1%. Thus, if greater tumor hypoxia correlates with a better response to HAP-mediated anti-cancer therapy, then this variability in tumor hypoxia will translate into a variable response to HAP anti-cancer therapy.

Enolase enzymes are encoded by three genes (ENO1, ENO2 and ENO3) and can produce multiple forms of enolase enzymes, including α-enolase (ENO1), γ-enolase (ENO2) and β-enolase (ENO3) (Capello et al., 2011, FEBS J. 278: 1064-1074; incorporated herein by reference). Enolase enzymes are glycolytic enzymes that catalyze the conversion of 2-phosphoglycerate to phosphoenolpyruvate. They can also localize to cytoplasmic membrane, acting as receptors for plasminogen and be secreted into the blood where serum levels can be measured. A serum-based immunoassay for ENO2 (NSE) is used in the diagnosis of small cell lung cancer, and other neural crest derived tumors and multiple immunoassay formats are available to measure ENO2 (Kasprzak et al., 2007, Pol J Pathol. 58: 23-33, incorporated herein by reference). US 2004/0219572 is directed to markers for the diagnosis of pancreatic cancer, including alpha-enolase, which is incorporated herein by reference. ENO1 and ENO2 are hypoxia-induced genes and the glycolytic activity of the encoded enzymes is thought to play a role in the altered cellular metabolism and survival of hypoxic cancer cells. Hypoxia results in a number of biological responses mediated by hypoxia signal transduction pathways. Two of the primary hypoxia signal transduction pathways are the HIF (hypoxia inducible factor) pathway and the UPR (unfolded protein response) pathway. The HIF-1 transcription factor, the master control factor for the hypoxic response in cells, is believed to regulate the expression of ENO1 and ENO2 since both genes contain HIF-1 transcription factor binding sites in their promoter regions (Tanimoto et al., 2010, HUGO J 4:35-48). Further enolase-related matter is described in US 2007/0077583, US 2010/0028907, US 2012/0164146 and Diaz-Ramos et al., 2012, J Biomed Biotech 2012: 1-12), each of which is incorporated herein by reference.

There remains a need for new methods of determining whether a cancer patient is likely to respond favorably to treatment with hypoxia-activated achiral phosphoramide mustards, such as TH-302, and/or to treat such patients. The present invention meets these needs.

SUMMARY OF THE INVENTION

The present invention arises out of the discovery that a cancer patient with high enolase level is more likely to respond favorably to HAP anti-cancer therapy than a cancer patient with a lower enolase level.

Thus, in a first aspect, the present invention provides a method for treating cancer comprising the steps of measuring enolase levels in a sample isolated from the patient, and administering a hypoxia-activated prodrug only if the enolase level measured is equal to or greater than a predetermined reference level, such as about 1.8 ng/ml. Enolase protein in a serum or plasma sample, as may be measured, for example or without limitation, using a bead-based suspension immunoassay, an ELISA, or another assay format to measure a serum analyte from blood serum or plasma. In one embodiment, a HAP is administered only if the measured enolase level is equal or greater than about 2 ng/ml (e.g., 2.3 ng/ml) protein in a serum sample. In one embodiment, a HAP is administered only if the measured enolase level is equal or greater than about 3 ng/ml (e.g., 3.2 ng/ml) protein in a serum sample. In one embodiment, a HAP is administered only if the measured enolase level is equal or greater than about 4 ng/ml, 5 ng/ml, 6 ng/ml, 7 ng/ml, 8 ng/ml, 9 ng/ml, 10 ng/ml, 11 ng/ml, 12 ng/ml, 13 ng/ml, 14 ng/ml, 15 ng/ml, 16 ng/ml, 17 ng/ml, 18 ng/ml or 19 ng/ml protein in a serum sample. In one embodiment, a HAP is administered only if the measured enolase level is equal or greater than about 20 ng/ml (e.g., 20.3913 ng/ml) protein in a serum sample. In one embodiment, a HAP is administered only if the measured enolase level is equal or greater than about 25 ng/ml, 30 ng/ml, 35 ng/ml, 40 ng/ml, 45 ng/ml, 50 ng/ml, 55 ng/ml, 60 ng/ml, 65 ng/ml, 70 ng/ml, 75 ng/ml, 80 ng/ml, 85 ng/ml, 90 ng/ml, 95 ng/ml, 100 ng/ml, 150 ng/ml, 200 ng/ml or 300 ng/ml protein in a serum sample. Thus, in one embodiment the enolase level is measured based on the amount of enolase protein in a serum sample. In another embodiment, the enolase level is measured based on the amount of enolase RNA in the sample. In a preferred embodiment, the enolase RNA is enolase mRNA, i.e., messenger RNA. In another preferred embodiment, the enolase RNA level is determined relative to a control sample, e.g. as Log 2 value. More preferably, the predetermined value is 5.0 Log 2.

In other embodiments, the sample is a plasma, serum, whole blood or pancreatic juice sample, or a sample derived from a tumor biopsy, such as tumor lysate or tumor tissue, and the enolase level is compared to a reference enolase level of predetermined value. The reference enolase level is determined using a reference population, which may be a population of healthy individuals, or a population of cancer patients, or patient-derived xenograft (PDX) xenograft models, or any combination thereof. The reference enolase level, the level at which HAP therapy is indicated for a patient and any others with equal to or higher enolase levels, may be, for example and without limitation, the median enolase level in a reference population or some multiple of that median, such as two or three times the median enolase. The predetermined value provided above were obtained using tumor samples obtained from patients in which enolase levels were measured using a bead-based suspension immunoassay format marketed by AssayGate, Inc., Ijamsville, Md. While similar values would be obtained using other methods and certain other sample times (blood plasma, for example), any change of sample source or enolase assay warrants additional testing to ensure that no adjustment of the predetermined value will improve results based on the different sampling or testing method employed.

The present invention involves methods that measure the expression level of enolase in the tumor by several possible methods, including RNA expression analysis (e.g., qRT-PCR, in-situ hybridization, etc.), methods of protein expression (e.g., western blotting, immunohistochemisty, FACS analysis of tumor lysates, or methods of detecting enolase protein or protein fragments in the blood). In one embodiment, the enolase levels are determined using a microarray. In other embodiments, other methods of measuring enolase levels are used. Non-limiting methods for assaying enolase include, quantitative western blots, immunohistochemistry (employing enolase antibodies) or histochemistry (employing enzyme substrates) of patient samples, including samples derived from tumor biopsies, core biopsies, and needle aspirates. In one preferred embodiment, the enolase levels are determined using a bead-based suspension immunoassay format or an ELISA.

In various embodiments, the HAP administered to the patient is TH-302.

BRIEF DESCRIPTION OF THE FIGURES

FIG. 1 shows PFS (FIG. 1A) and OS (FIG. 1B) results, respectively, for 121 chemotherapy naïve patients with locally advanced unresectable or metastatic pancreatic adenocarcinoma undergoing treatment with Gem (n=56) Gem+TH-302 340 mg/m$^2$ (n=65), graphed by ENO2 levels, using the median of 20.3913 ng/ml as the cut-off for placing patients in the high or low ENO2 groups.

FIG. 2 shows PFS (FIG. 2A) and OS (FIG. 2B) results, respectively, for 65 chemotherapy naïve patients with locally advanced unresectable or metastatic pancreatic adenocarcinoma undergoing treatment with Gem+TH-302 340 mg/m$^2$, graphed by ENO1 levels, using 1.8 ng/ml as the cut-off for placing patients in high vs. low ENO1 groups. FIG. 2 also shows results for the same set of patient data summarized in FIGS. 2A and 2B, but graphed using the ENO1 level of 2.3 ng/ml as the cut-off for placing patients in the upper third vs. lower two thirds of ENO1 levels (FIG. 2C) as well as ENO1 level of 3.2 ng/ml as the cut-off for placing patients in the upper quartile vs. lower three quartiles of ENO1 levels (FIG. 2D), respectively.

DETAILED DESCRIPTION OF THE INVENTION

Figure 1A:
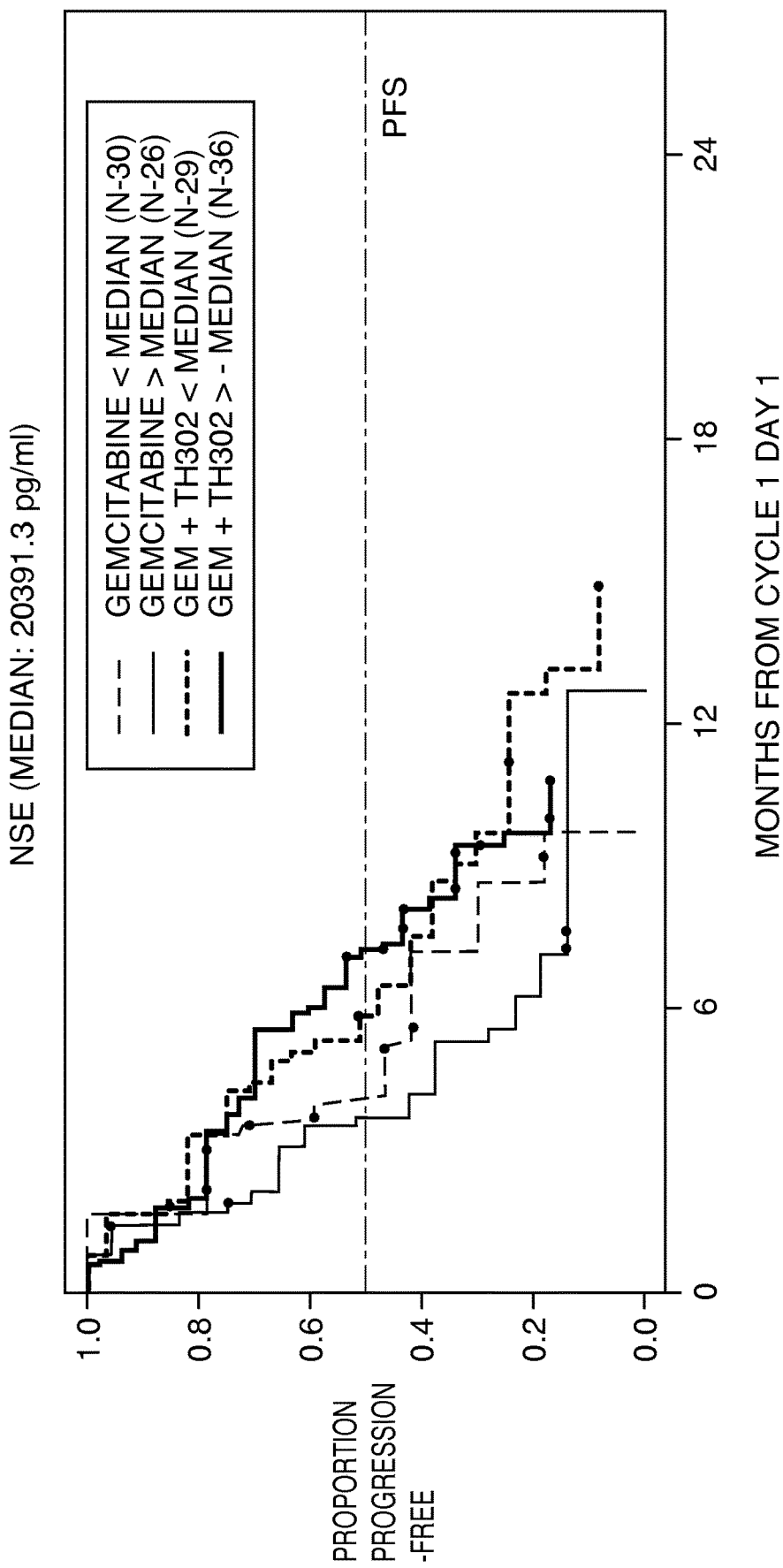
FIG. 1 shows Kaplan-Meier Progression Free Survival (PFS) (FIG. 1A) and Overall Survival (OS) (FIG. 1B) graphs for patients receiving Gemcitabine (Gem) or Gem+TH-302 340 mg/m$^2$ based on the median level of ENO2 (NSE, neural-specific enolase). In detail.

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

"About" as used herein is used to provide flexibility to a numerical range endpoint by providing that a given value may be "a little above" or "a little below" the endpoint accounting for variations one might see in measurements taken among different instruments, samples, and sample preparations. In one aspect, "about" refers to ±20% of a quantity and includes, but is not limited to, +15%, +10%, and +5% of the quantity.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Biomarkers" generally refers to biological molecules, and quantitative and qualitative measurements of the same, that are indicative of a disease state. "Prognostic biomarkers" correlate with disease outcome, independent of therapy. For example, tumor hypoxia is a negative prognostic marker—the higher the tumor hypoxia, the higher the likelihood that the outcome of the disease will be negative. "Predictive biomarkers" indicate whether a patient is likely to respond positively to a particular therapy. For example, HER2 profiling is commonly used in breast cancer patients to determine if those patients are likely to respond to Herceptin (trastuzumab, Genentech). "Response biomarkers" provide a measure of the response to a therapy and so provide an indication of whether a therapy is working. For example, decreasing levels of prostate specific antigen (PSA) generally indicate that anti-cancer therapy for a prostate cancer patient is working.

"Blood" refers to blood which includes all components of blood circulating in a subject including, but not limited to, red blood cells, white blood cells, plasma, clotting factors, small proteins, platelets and/or cryoprecipitate. This is typically the type of blood which is donated when a human patent gives blood. Plasma is known in the art as the yellow liquid component of blood, in which the blood cells in whole blood are typically suspended. It makes up about 55% of the total blood volume. Blood plasma can be prepared by spinning a tube of fresh blood containing an anti-coagulant in a centrifuge until the blood cells fall to the bottom of the tube. The blood plasma is then poured or drawn off. Blood plasma has a density of approximately 1025 kg/m$^3$, or 1.025 kg/l. Serum differs from plasma, the liquid portion of normal unclotted blood containing the red and white cells and platelets. Serum is known in the art as the clear liquid that can be separated from clotted blood. Serum is the component that is neither a blood cell (serum does not contain white or red blood cells) nor a clotting factor. It is the blood plasma not including the fibrinogens that help in the formation of blood clots. It is the clot that makes the difference between serum and plasma.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gall bladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythemia vera, primary brain tumor, small cell lung tumor, non-small cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Clinical outcome", "clinical parameter", "clinical response", or "clinical endpoint" refers to any clinical observation or measurement relating to a patient's reaction to a therapy. Non-limiting examples of clinical outcomes include tumor response (TR), overall survival (OS), progression free survival (PFS), disease free survival, time to tumor recurrence (TTR), time to tumor progression (TTP), relative risk (RR), toxicity or side effect.

"Comprising", as used herein, is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

"Having the same cancer" refers to comparing one patient to another or alternatively, one patient population, which may be a reference population, to another patient population. For example, the two patients or patient population will each have or be suffering from colon cancer.

"Hypoxia activated prodrug" or "HAP" refers to a prodrug wherein the prodrug is less active or inactive, relative to the corresponding drug, and comprises the drug and one or more bioreducible groups. HAPs include prodrugs that are activated by a variety of reducing agents and reducing enzymes, including without limitation single electron transferring enzymes (such as cytochrome P450 reductases) and two electron transferring (or hydride transferring) enzymes. In some embodiments, HAPs are 2-nitroimidazole triggered hypoxia-activated prodrugs. Examples of HAPs include, without limitation, TH-302 and TH-281. Methods of synthesizing TH-302 are described in US 2010/0137254 and US 2010/0183742, incorporated herein by reference.

"In-situ hybridization" is a methodology for determining the presence of or the copy number of a gene in a sample, for example, fluorescence in situ hybridization (FISH). Generally, in-situ hybridization comprises the following major steps: (1) fixation of tissue or biological structure to be analyzed; (2) pre-hybridization treatment of the biological structure to increase accessibility of target nucleic acid, and to reduce non-specific binding; (3) hybridization of the mixture of nucleic acids to the nucleic acid in the biological structure or tissue; (4) post-hybridization washes to remove nucleic acid fragments not bound in the hybridization; and (5) detection of the hybridized nucleic acid fragments. The probes used in such applications are typically labeled, for example, with radioisotopes or fluorescent reporters. Preferred probes are sufficiently long, for example, from about 50, 100 or 200 nucleotides (nt) to about 1000 or more nucleotides, to enable specific hybridization with the target nucleic acid(s) under stringent conditions. Here, hybridization with cDNA can be accomplished, preferably by incubating at 50 to 80° C. for 10 to 20 hours, more preferably about 65° C. for 10 to 20 hours.

"Isolated" refers to molecules or biological or cellular materials being substantially free from other materials. In one aspect, the term "isolated" refers to nucleic acid, such as DNA or RNA, or protein or polypeptide, or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

"Microarray" refers to nucleotide arrays that can be used to detect biomolecules, for instance to measure gene expression. "Array", "slide" and "(DNA) chip" are used interchangeably in this disclosure. A microarray usually comprises a basal plate, e.g. made of slide glass, silicone, or the like, and DNA fragments immobilized as an array on this basal plate. With this microarray, DNAs and/or RNAs contained in a sample can be detected by hybridizing them with the DNA fragments immobilized on the basal plate. Since the DNA and/or RNA within the sample could be radiolabeled or fluorescently labeled, detection with radio imaging scanner, fluorescence imaging scanner, or the like is possible. Various kinds of arrays are made in research and manufacturing facilities worldwide, some of which are available commercially. There are, for example, two main kinds of nucleotide arrays that differ in the manner in which the nucleic acid materials are placed onto the array substrate: spotted arrays and in-situ synthesized arrays. One of the most widely used oligonucleotide arrays is GeneChip made by Affymetrix, Inc. The oligonucleotide probes have a length of 10 to 50 nucleotides (nt), preferably 15 to 30 nt, more preferably 20 to 25 nt. They are synthesized in-silico on the array substrate. These arrays tend to achieve high densities, e.g. more than 40,000 genes per $cm^2$. The spotted arrays, on the other hand, tend to have lower densities, but the probes, typically partial cDNA molecules, usually are much longer than 25 nucleotides. A representative type of spotted cDNA array is LifeArray made by Incyte Genomics. Pre-synthesized and amplified cDNA sequences are attached to the substrate of these kinds of arrays.

"Pancreatic juice sample" refers to pancreatic secretions and isolates of such secretions obtained by a physician.

"Patient" and "subject" are used interchangeably to refer to a mammal in need of treatment for cancer or other hyperproliferative disease. Generally, the patient is a human. Generally, the patient is a human diagnosed with cancer. In certain embodiments a "patient" or "subject" may refer to a non-human mammal such as a non-human primate, a dog, cat, rabbit, pig, mouse or rat such as animals used in screening, characterizing, and evaluating drugs and therapies.

"Physiologically acceptable salt" refers to an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body. While the said compounds according to the invention can be used in their final non-salt form, the present invention also encompasses the use of these compounds in the form of their pharmaceutically acceptable salts, which can be derived from various organic and inorganic acids and bases by procedures known in the art.

"Polymerase Chain Reaction" or "PCR" is an amplification-based assay used to measure the copy number of the gene. In such assays, the corresponding nucleic acid sequences act as a template in an amplification reaction. In a quantitative amplification, the amount of amplification product will be proportional to the amount of template in the original sample. Comparison to appropriate controls provides a measure of the copy number of the gene, corresponding to the specific probe used, according to the principle known in the art.

A "predetermined value" for enolase as used herein, is so chosen that a patient with a level of enolase higher than the predetermined value is likely to experience a more desirable clinical outcome than patients with levels of enolase lower than the predetermined value, or vice-versa. Levels of proteins and/or RNA, such as those disclosed in the present invention, are associated with clinical outcomes. One of skill in the art can determine such predetermined values by measuring levels of enolase in a patient population to provide a predetermined value. Optionally, a predetermined value for enolase level in one patient population can be compared to that from another to optimize the predetermined value to provide higher predictive value. In various embodiments, a predetermined value refers to value(s) that best separate patients into a group with more desirable clinical outcomes and a group with less desirable clinical outcomes. Such predetermined value(s) can be mathematically or statistically determined with methods well known in the art in view of this disclosure.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"QnD" or "qnd" refers to drug administration once every n days. For example, OD (or qd) refers to once every day or once daily dosing, Q2D (or q2d) refers to a dosing once every two days, Q7D refers to a dosing once every 7 days or once a week.

"Reduction" of a symptom or symptoms (and grammatical equivalents of this phrase) refers to decreasing the severity or frequency of the symptom(s), or elimination of the symptom(s).

"Solid tumor" refers to a cancer other than leukemia. Solid tumor refers to solid tumors including, but are not limited to, metastatic tumors in bone, brain, liver, lungs, lymph node, pancreas, prostate, skin and soft tissue (sarcoma).

"Suitable for a therapy" or "suitably treated with a therapy" shall mean that the patient is likely to exhibit one or more desirable clinical outcome as compared to patients having the same cancer and receiving the same therapy but possessing a different characteristic that is under consideration for the purpose of the comparison. In one aspect, the characteristic under consideration is a genetic polymorphism or a somatic mutation. In another aspect, the characteristic under consideration is expression level of a gene or a polypeptide. In one aspect, a more desirable clinical outcome is relatively higher likelihood of or relatively better tumor response such as tumor load reduction. In another aspect, a more desirable clinical outcome is relatively longer overall survival. In yet another aspect, a more desirable clinical outcome is relatively longer progression free survival or time to tumor progression. In yet another aspect, a more desirable clinical outcome is relatively longer disease free survival. In another aspect, a more desirable clinical outcome is relative reduction or delay in tumor recurrence. In another aspect, a more desirable clinical outcome is relatively decreased metastasis. In another aspect, a more desirable clinical outcome is relatively lower relative risk. In yet another aspect, a more desirable clinical outcome is relatively reduced toxicity or side effects. In some embodiments, more than one clinical outcome are considered simultaneously. In one such aspect, a patient possessing a characteristic, such as a genotype of a genetic polymorphism, may exhibit more than one more desirable clinical outcomes as compared to patients having the same cancer and receiving the same therapy but not possessing the characteristic. As defined herein, the patient is considered suitable for the therapy. In another such aspect, a patient possessing a characteristic may exhibit one or more desirable clinical outcome but simultaneously exhibit one or more less desirable clinical outcome. The clinical outcomes will then be considered collectively, and a decision as to whether the patient is suitable for the therapy will be made accordingly, taking into account the patient's specific situation and the relevance of the clinical outcomes. In some embodiments, progression free survival or overall survival is weighted more heavily than tumor response in a collective decision making.

"Therapeutically effective amount" of a drug refers to an amount of a drug that, when administered to a patient with cancer or other hyperproliferative disease, will have the intended therapeutic effect, e.g., alleviation, amelioration, palliation or elimination of one or more manifestations of cancer or another hyperproliferative disease in the patient. A therapeutic effect does not necessarily occur by administration of one dose, and may occur only after administration of a series of doses. Thus, a therapeutically effective amount may be administered in one or more administrations.

"Treating" or "treatment of" a condition or patient refers to taking steps to obtain beneficial or desired results, including clinical results. For purposes of this invention, beneficial or desired clinical results include, but are not limited to, alleviation or amelioration of one or more symptoms of cancer or other hyperproliferative disease; diminishment of extent of disease; delay or slowing of disease progression; amelioration, palliation, or stabilization of the disease state; or other beneficial results. Treatment of cancer may, in some cases, result in partial response or stable disease.

"Tumor" refers to an abnormal growth of tissue resulting from uncontrolled, progressive multiplication of cells and serving no physiological function. A tumor is also known as a neoplasm.

When a marker, such as enolase, is "used as a basis" for identifying or selecting a patient for a treatment described herein, the marker can be measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of a biomarker in a clinical setting is a clear indication that this parameter was used as a basis for initiating, continuing, adjusting and/or ceasing administration of the treatments described herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Some abbreviations used in the description include:
CI: Confidence interval
ENO1: Enolase 1, α-enolase
ENO2: Enolase 2, γ-enolase, neural-specific enolase (NSE)
ENO3: Enolase 3, β-enolase
HAP(s): Hypoxia Activated Prodrug(s)
Gem: Gemcitabine
HR: Hazard ratio
PFS: Progression free survival
OS: Overall survival Descriptive Embodiments The disclosure further provides diagnostic, predictive, prognostic and therapeutic methods, which are based, at least in part, on determination of the identity of the expression level of a marker of interest. In particular, the amount of enolase in a cancer patient sample can be used to predict whether the patient is likely to respond favorably to cancer therapy utilizing a hypoxia-activated prodrug of formula (I).

It shall also be understood that variants, mutants, parts or homologous protein sequences of enolase having the same function, are included in the scope of definition as well as protection. Possible alterations comprise deletion, insertion, substitution, modification and addition of at least one amino acid. Physiological fragments, secondary modifications, species-dependent alterations as well as allelic variants of enolase are also encompassed by the present invention. Preferably, the homology amounts to at least 85%, more preferably at least 95%, most preferably at least 98%. Enolases may be named in different way but can be easily and uniquely assigned by the accession numbers (e.g., P06733, P09104 and P13929), which are generally accepted and registered in data bases, such as UniProt.

In the meaning of the invention, the enolase can be any isoform in the art. Three subunits (α, β, γ), each encoded by a separate gene, can combine to form five different isoenzymes known: αα, αβ, αγ, ββ and γγ. In one embodiment, ENO1 is used in the meaning of the invention. ENO1 (enolase 1, αα, non-neuronal enolase [NNE], α-enolase [ENO A]) is found in most tissues. Overexpression is described, e.g., in NSCLC, H&N, breast cancer, CRC, pancreatic cancer, melanoma and HCC. It is a hypoxia-inducible, HIF-1α target gene. In one embodiment, ENO2 is used in the meaning of the invention. ENO2 (enolase 2, γγ, neuron-specific enolase [NSE], γ-enolase) is e.g. overexpressed in SCLC, neuroblastoma, PNET and neuroendocrine tumors. It is a diagnostic marker for SCLC follow-up diagnosis based on multiple assays commercially available. It is also described as a hypoxia-inducible, HIF-1a target gene in some cell models. In one embodiment, ENO3 is used in the meaning of the invention. ENO3 (enolase 3, ββ, muscle specific enolase [MSE]) is e.g. overexpressed in rhabdomyosarcoma. A link to hypoxia and cancer is not established. In one preferred embodiment, the enolase is selected from the group consisting of ENO1 (α-enolase), ENO2 (γ-enolase) and ENO3 (β-enolase). In one preferred embodiment, the enolase is ENO1 (α-enolase), ENO2 (γ-enolase) and/or ENO3 (β-enolase), more preferably ENO1 (α-enolase) and/or ENO2 (γ-enolase), most preferably ENO1 (α-enolase).

Thus, information obtained using the diagnostic assays described herein is useful for determining if a subject is suitable for cancer treatment of a given type. Based on the predictive information obtained, a doctor can recommend a therapeutic protocol, which may include administration of a hypoxia-activated prodrug, useful for reducing the malignant mass or tumor in the patient or treat cancer in the individual.

In one aspect, a method is provided for treating cancer in a patient, comprising the steps of determining that an enolase RNA or protein level in a cancer sample isolated from said patient exceeds a predetermined level and administering to said patient a hypoxia-activated prodrug of formula (I)

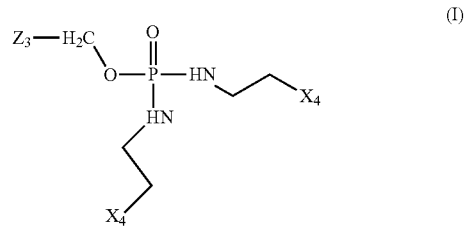

wherein $Z_3$ is selected from the group consisting of:

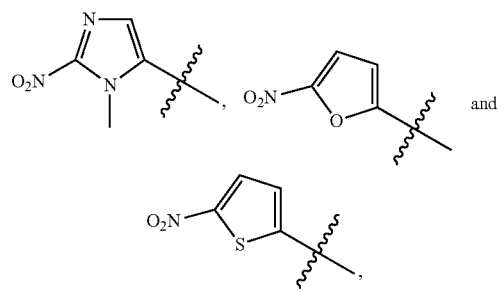

and $X_4$ is Cl or Br, or a physiologically acceptable salt thereof.

In another aspect, a method is provided for predicting the likelihood that a patient suffering from cancer, who is a candidate for treatment with a hypoxia-activated prodrug of formula (I), as defined above, will respond to the treatment with said prodrug, comprising the determination of the expression level of a prognostic gene or expression product thereof, which is an enolase, in a cancer sample obtained from said patient, wherein a higher expression indicates that the patient is likely to respond to said treatment compared to a predetermined value.

Still another aspect of the invention is a method, preferably an in-vitro method, for predicting the likelihood that a patient suffering from cancer will respond therapeutically to the treatment with a hypoxia-activated prodrug of formula (I), as defined above, comprising the steps of (i) measuring in a biopsy tissue sample from tumor tissue or plasma of said patient the expression level of an enolase biomarker on protein basis, (ii) exposing said patient, preferably ex-vivo a tissue sample from tumor or plasma of said patient, to said prodrug, and (iii) measuring in said patient or exposed tissue sample of step (ii) the expression level of said biomarker specified in step (i) along with calculating the differences in expression levels measured in steps (i) and (iii), wherein a decrease in the expression level of said biomarker obtained in this step (iii) compared to step (i) indicates an increased likelihood that said patient will respond therapeutically to the treatment with said prodrug.

The reference value is defined by one or more of a specific functional or clinical property, and/or a specific, genetic or protein expression profile obtained from a reference patient or reference patient group. Said reference patient or patient group that does not express or express less gene product compared to the candidate patient. The reference value is an expression threshold value which is individually constituted or defined by specific clinical response parameters to be determined or by specific pre-treatment or treatment conditions. Suitable clinical response parameters are the progression free survival time (PFS), overall survival time (OS), partial response (PR), stable response (SR), progressive disease (PD) or combinations thereof.

For example, tissue or plasma samples are taken from the patient before treatment with the hypoxia-activated prodrug and optionally on treatment with the hypoxia-activated prodrug. The expression levels obtained on treatment are compared with the values obtained before starting treatment of said patient.

The information obtained may also be prognostic, in that it can indicate whether a patient has responded favorably or unfavorably to cancer therapy. Generally, if enolase levels rise after administration of a cancer therapy, the therapy may not be as efficacious as other therapies, and if enolase levels decline after therapy, the therapy is efficacious.

In one aspect, the invention also relates to a method for monitoring the likelihood of response to a treatment of cancer, which are mediated and/or propagated by hypoxia, wherein the enolase RNA or protein level is determined in a cancer sample withdrawn from a patient in need of such treatment with a hypoxia-activated prodrug of formula (I), as defined above, administered to said patient, wherein a decrease in enolase relative to a predetermined level of enolase in a cancer sample indicates an increased likelihood that said mammal responds to the treatment with said hypoxia-activated prodrug.

The identification of enolase provides a powerful tool for assessing the progression of a state, condition or treatment.

The present invention can be used as a clinical marker to monitor efficacy of a compound of formula (I) on each patient individually. Specifically, enolase can be identified in a patient prior to an event, such as surgery, the onset of a therapeutic regime, or the completion of a therapeutic regime, to provide a base line result. This base-line can then be compared with the result obtained using identical methods either during or after such event. This information can be used for both diagnostic and prognostic purposes. The information about the clinical marker can be additionally used to optimize the dosage and the regimen of an active compound by monitoring the decrease of enolase in the subject's biological sample. Furthermore, the method of the present invention can be used to find a therapeutically effective compound and/or a therapeutically effective amount or regimen for the selected compound, thereby individually selecting and optimizing a therapy for a patient.

A patient's likely clinical outcome following a clinical procedure such as a therapy or surgery can be expressed in relative terms. For example, a patient having a particular enolase expression level who receives HAP therapy may experience relatively longer overall survival than a patient or patients not having the enolase expression level who receive HAP therapy. The patient having the particular enolase expression level, alternatively, can be considered as likely to survive if administered HAP therapy. Similarly, a patient having a particular expression level who receives HAP therapy may experience relatively longer progression free survival, or time to tumor progression, than a patient or patients not having the enolase expression level who receive HAP therapy. The patient having the particular enolase expression level, alternatively, can be considered as not likely to suffer tumor progression if administered HAP therapy. Further, a patient not having a particular enolase expression level who receives HAP therapy may experience relatively shorter time to tumor recurrence than a patient or patients having the expression level who receive HAP therapy. The patient having the particular enolase expression level, alternatively, can be considered as not likely to suffer tumor recurrence if administered HAP therapy. It is still another example that a patient having a particular expression level if administered HAP therapy may experience a relatively more complete response or partial response than a patient or patients not having the genotype or expression level who receive HAP therapy. The patient having the particular genotype or expression level, alternatively, can be considered as likely to respond to HAP therapy. Accordingly, a patient that is likely to survive, or not likely to suffer tumor progression, or not likely to suffer tumor recurrence, or likely to respond following a clinical procedure is considered suitable for the clinical procedure, treatment with a HAP.

It is to be understood that information obtained using the diagnostic assays described herein may be used alone or in combination with other information, such as, but not limited to, expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient, etc. When used in combination with other information, on the other hand, the information obtained using the diagnostic assays described herein is useful in aiding in the determination or identification of clinical outcome of a treatment, aiding in the selection of a patient for a treatment, or aiding in the treatment of a patient and the like. In a particular aspect, the expression level can be used in a diagnostic panel each of which contributes to the final diagnosis, prognosis, or treatment selected for a patient.

Thus, object of the invention is the use of enolase as biomarker for a hypoxia-activated prodrug of formula (I), as defined above and intended to be used for the treatment of cancer. The intended use is particularly a first-line treatment, and the prodrug is administered in mono-therapy. In an alternative embodiment of the intended use, said prodrug is combined with another chemotherapeutic agent, and said patient has developed chemo-refractory cancer.

The present invention arises out of the discovery that a cancer patient with high enolase level is more likely to respond favorably to HAP anti-cancer therapy than a cancer patient with a lower enolase level.

Diagnostic Methods

Thus, in one aspect, a method is provided for aiding in the selection of or selecting a hypoxia-activated prodrug therapy for a cancer patient, comprising, or alternatively consisting essentially of, or yet further consisting of, determining an enolase RNA or protein level in a sample isolated from the patient, wherein the hypoxia-activated prodrug therapy is selected for the patient if the level is equal to or exceeds a predetermined level (value) or the hypoxia-activated prodrug therapy is not selected if the level is below the predetermined level (value), wherein the hypoxia-activated prodrug therapy comprises, or alternatively consists essentially of, or yet further consists of a hypoxia-activated prodrug of formula (I)

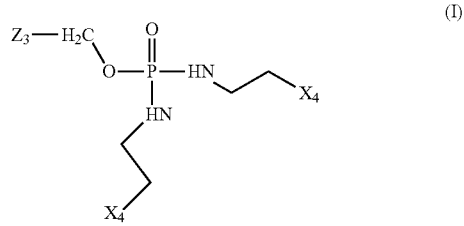

(I)

wherein $Z_3$ is selected from the group consisting of:

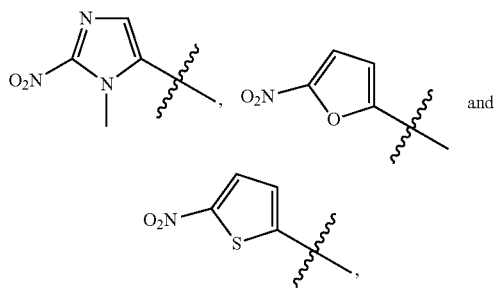

and $X_4$ is Cl or Br, or a physiologically acceptable salt thereof.

In one aspect, the enolase RNA level is determined relative to a control sample as Log 2 value with the predetermined value of 5.0 Log 2. In one aspect, the predetermined enolase protein level is about 2 ng/ml±20%, preferably about 3 ng/ml±10%, more preferably about 20 ng/ml±5%, most preferably about 25 ng/ml±5%, highly preferably about 30 ng/ml±5%, particularly highly preferably about 50 ng/ml±5%. In one aspect, the therapy is selected for patients exhibiting progression-free survival as compared to similarly situated patients with the marker and did not receive the HAP therapy.

In one aspect, the hypoxia-activated prodrug therapy comprises, or alternatively consists essentially of, or yet further consists of (2-bromoethyl)({[(2-bromoethyl)amino][(2-nitro-3-methylimidazol-4-yl)methoxy]phosphoryl}) amine (TH-302) or (2-chloroethyl)({[(2-chloroethyl)amino][(2-nitro-3-methylimidazol-4-yl)methoxy]phosphoryl}) amine (TH-281).

In some embodiments, cancer patients that benefit from the diagnostic method include those suffering from various solid tumors, for example and without limitation, hypoxic solid tumors, blood cancers, and the like. In some embodiments, patients that benefit from the diagnostic method include those suffering from various solid tumors and undergoing monotherapy with TH-302. In a preferred embodiment of the invention, patients that benefit from the diagnostic method include those suffering from pancreatic cancer.

In one aspect, the enolase is ENO1 (α-enolase), ENO2 (γ-enolase) and/or ENO3 (β-enolase), preferably ENO1 (α-enolase) and/or ENO2 (γ-enolase), more preferably ENO1 (α-enolase).

Any suitable sample can be used for the method. Non-limiting examples of such include one or more of a serum sample, plasma sample, whole blood, pancreatic juice sample, tissue sample, tumor lysate or a tumor sample, which can be a isolated from a needle biopsy, core biopsy and needle aspirate.

Any suitable method can be used to measure the enolase protein, RNA, or other suitable read-outs for enolase levels, examples of which are described herein and/or are well known to the skilled artisan. In some embodiments, determining the level of an enolase comprises determining the expression of enolase, such as, e.g., by determining the enolase mRNA or enolase protein concentration in a patient sample. To this extent, mRNA of the sample can be isolated, if necessary, after adequate sample preparation steps, e.g. tissue homogenization, and hybridized with marker specific probes, in particular on a microarray platform with or without amplification, or primers for PCR-based detection methods, e.g. PCR extension labeling with probes specific for a portion of the marker mRNA.

In an embodiment of the invention, a DNA or RNA array comprises an arrangement of polynucleotides presented by or hybridizing to the enolase gene immobilized on a solid surface.

In further embodiments, the level of enolase is determined by the polypeptide or protein concentration of the enolase, e.g., with enolase specific ligands, such as antibodies or specific binding partners. The binding event can, e.g., be detected by competitive or non-competitive methods, including the use of labeled ligand or enolase specific moieties, e.g., antibodies, or labeled competitive moieties, including a labeled enolase standard, which compete with marker proteins for the binding event. If the marker specific ligand is capable of forming a complex with the enolase, the complex formation can indicate expression of the enolase in the sample.

Although the biomarker of the invention exhibits a sensitivity that allows its exclusive use in the scope of the methods described herein, it is another embodiment of the invention to apply more biomarkers in addition to the enolase marker. Analyzing multiple biomarkers increases screening stability and reduces error rates by covering a broader spectrum of responses than low-plurality reporter assays. In a preferred embodiment of the present invention, the expression levels of at least two, three, four, five, six, seven, eight, nine or ten biomarkers are determined, including an enolase. In a more preferred embodiment of the invention, enolase is determined in connection with a second biomarker. The particular combination of at least two biomarkers refines the correction with cancer susceptibility.

This disclosure also provides a kit for determining if a hypoxia-activated prodrug therapy is suitable for treatment of a cancer patient, comprising means for determining a serum protein level of an enolase protein, or the expression level of enolase RNA, in a sample isolated from the patient and instructions for use. In a further aspect, the kit further comprises the HAP therapy with a hypoxia-activated prodrug of formula (I). In one aspect of the invention, the determination of a high enolase level indicates increased PFS or OS when the patient is treated with said prodrug.

In one embodiment of the kit, the means for determining the enolase RNA level are nucleic acid probes that are capable of specifically hybridizing under stringent conditions with enolases or gene products encoded by enolase genes or respective parts thereof. In a preferred embodiment of the kit, a diagnostic kit for real-time PCR amplification of the enolase biomarker is provided, comprising a first package comprising the DNA or RNA of one or more of the enolase, a second package comprising PCR primers which specifically hybridize with said DNA/RNA molecules of said first package, a third package comprising a well-plate or a respectively suitable container, and a fourth package comprising diagnostic means and solvents by means of which real-time PCR amplification can be carried out. In another embodiment of the kit, the means for determining the enolase protein level are antibodies with specific binding to enolase.

Therapeutic Methods

Thus, in one aspect, the present invention provides a method for treating cancer in a patient comprising the steps of measuring enolase levels in a sample isolated from the patient, and administering a hypoxia-activated prodrug only if the enolase level measured is equal to or greater than a predetermined reference level, wherein the hypoxia-activated prodrug comprises, or alternatively consists essentially of, or yet further consists of a hypoxia-activated prodrug of formula (I)

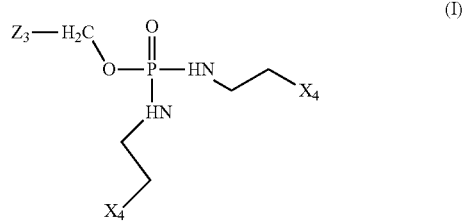

(I)

wherein $Z_3$ is selected from the group consisting of:

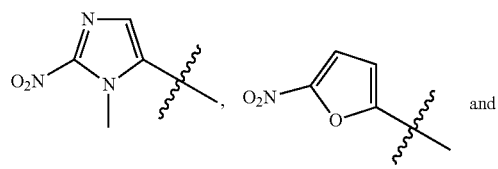

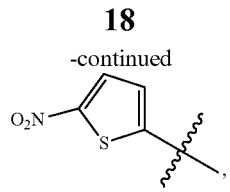

and $X_4$ is Cl or Br, or a physiologically acceptable salt thereof, or administering a cancer therapy other than a therapy comprising administration of said hypoxia-activated prodrug of formula (I) if such measured level does not exceed said predetermined value.

In another aspect, the present invention provides a hypoxia-activated prodrug of formula (I) as defined above, for use in a method of treatment of cancer, optionally in combination with another chemotherapy, in which the treatment is contra-indicated for cancer in which an enolase RNA or protein level is below a predetermined value or not present and the enolase RNA or protein levels are measured prior to making a decision to treat with a compound of formula (I), and such decision to treat is based on the levels measured. In this context, the term "contra-indicated or "non-responsive", which are used interchangeably herein, means that a patient will not have a response according to RECIST criteria, or will have a reduced survival than a similar patient having high enolase level (see US 2009/0202989, incorporated herein by reference).

In still another aspect, the invention provides a method for advertising a hypoxia-activated prodrug of formula (I), as defined above, to a target audience, the use of said prodrug for treating a patient with cancer based on measured expression of enolase biomarker. Promotion may be conducted by any means available. In some embodiments, the promotion is by a package insert accompanying a commercial formulation of the hypoxia-activated prodrug of formula (I) (such as TH-302). The promotion may also be by a package insert accompanying a commercial formulation of a second medicament (when treatment is a combination therapy with a hypoxia-activated prodrug of formula (I) and a second medicament). Promotion may be by written or oral communication to a physician or health care provider. In some embodiments, the promotion is by a package insert where the package insert provides instructions to receive therapy with the hypoxia-activated prodrug of formula (I) after measuring enolase levels, and in some embodiments, in combination with a second medicament. In some embodiments, the promotion is followed by the treatment of the patient with the hypoxia-activated prodrug of formula (I) with or without the second medicament. In some embodiments, the promotion is followed by the treatment of the patient with the second medicament with or without treatment with the hypoxia-activated prodrug of formula (I). In some embodiments, the package insert indicates that the hypoxia-activated prodrug of formula (I) is to be used to treat the patient if the patient's cancer sample expressed high enolase biomarker levels. In some embodiments, the package insert indicates that the hypoxia-activated prodrug of formula (I) is not to be used to treat the patient if the patient's cancer sample expresses low enolase biomarker levels. In some embodiments, high enolase biomarker levels means a measured enolase level that correlates with a likelihood of increased PFS and/or OS when the patient is treated with the hypoxia-activated prodrug of formula (I). In some embodiments, low enolase biomarker levels means a measured enolase level that correlates with a likelihood of decreased PFS and OS when the patient is treated with the hypoxia-activated prodrug of formula (I). In some embodiments, the PFS and/or OS is decreased relative to a patient who is not treated with the hypoxia-activated prodrug of formula (I). In some embodiments, the promotion is by a package insert where the package inset provides instructions to receive therapy with TH-302 after first measuring enolase levels. In some embodiments, the promotion is followed by the treatment of the patient with TH-302 with or without the second medicament. Further methods of advertising and instructing, or business methods applicable in accordance with the invention are described (for other drugs and biomarkers) in US 2012/0089541, which is incorporated herein by reference.

In one embodiment, the enolase level is measured based on the amount of enolase RNA in the sample. Preferably, the enolase RNA level is determined relative to a control sample, e.g., as Log 2 value. More preferably, the predetermined RNA level value is 5.0 Log 2. In another preferred embodiment, the predetermined protein level is about 2 ng/ml±20%, preferably about 3 ng/ml±10%, more preferably about 20 ng/ml±5%, most preferably about 25 ng/ml±5%, highly preferably about 30 ng/ml±5%, particularly highly preferably about 50 ng/ml±5%. In other words, a HAP is administered only if the measured enolase level is equal or greater than about the aforementioned predetermined protein levels. In various embodiments, the sample is a plasma, serum, whole blood, pancreatic juice or tumor tissue sample, preferably a serum sample. Using these values as the cut-off for dividing patients into high and low enolase level groups, one sees an even more dramatic example of the predictive value of enolase levels in determining whether a patient will respond to TH-302 or other HAP therapy with a compound of formula (I). It is surprisingly demonstrated that higher enolase levels correlated to a better response to TH-302 (see FIGS. 1 and 2).

In one important embodiment, the HAP is (2-bromoethyl)({[(2-bromoethyl)amino][(2-nitro-3-methylimidazol-4-yl)methoxy]phosphoryl})amine (TH-302). In another embodiment, the hypoxia-activated prodrug comprises (2-chloroethyl)({[(2-chloroethyl)amino][(2-nitro-3-methylimidazol-4-yl)methoxy]phosphoryl})amine (TH-281). In one embodiment, the cancer patient is suffering from pancreatic cancer. In one embodiment, a patient sample is one or more of a plasma sample, serum sample, whole blood sample, pancreatic juice sample, tissue sample, tumor sample or tumor lysate. In all embodiments, enolase levels measured in a sample from a patient to be treated are used to inform treatment decisions for that patient with compounds of formula (I).

In one embodiment, the enolase is ENO1 (α-enolase), ENO2 (γ-enolase) and/or ENO3 (β-enolase), preferably ENO1 (α-enolase) and/or ENO2 (γ-enolase), more preferably ENO1 (α-enolase).

In another embodiment, the hypoxia-activated prodrug is administered in an amount of about 100 mg/m$^2$ to about 700 mg/m$^2$ to the patient in need of cancer therapy, preferably about 200 mg/m$^2$ to about 575 mg/m$^2$, more preferably about 240 mg/m$^2$ to about 340 mg/m$^2$. An individual patient's surface area can be determined using routine methods known to oncologists and other medical providers. For an adult human, a dose of 1 mg/m$^2$ of an active agent (drug) is equal to about 1.7 mg of that agent or drug per patient (i.e., the prototypical adult human has 1.7 m$^2$ of surface area). Therefore, for example, 100 mg/m$^2$ of a drug is equal to about 170 mg of that drug per patient. Further preferred dosage regimes in the meaning of the invention are disclosed in US 2013/0202716, which is incorporated herein by reference.

The hypoxia-activated prodrug can be adapted for administration via any desired suitable method, for example by oral (including buccal or sublingual), rectal, nasal, topical (including buccal, sublingual or transdermal), vaginal or parenteral (including intravenous, intraperitoneal, subcutaneous, intra-muscular or intradermal) methods. A preferred route of administration is a parenteral method, more preferably intravenous, intraperitoneal or subcutaneous injection, most preferably intravenous injection.

In another preferred embodiment of the invention, the hypoxia-activated prodrug is administered intravenously in an amount of about 240 mg/m$^2$ to about 340 mg/m$^2$ to the patient in need of cancer therapy, more preferably, whether intravenously or not, in an amount of 240 mg/m$^2$ to 340 mg/m$^2$, most preferably intravenously in an amount of about 240 mg/m$^2$ or about 340 mg/m$^2$, highly preferably, whether intravenously or not, in an amount of about 240 mg/m$^2$ or about 340 mg/m$^2$, particularly highly preferably, whether intravenously or not, in an amount of 340 mg/m$^2$.

In another preferred embodiment, the hypoxia-activated prodrug is administered in combination with an anticancer drug that is not a hypoxia-activated prodrug after enolase levels are measured and determined to warrant therapy with a HAP. Preferred non-HAPs for use with HAPs are gemcitabine, gemcitabine in combination with nab-paclitaxel (Abraxane), or FOLFIRINOX. In particular, WO 2013/126539, which is incorporated herein by reference, provides medicines and technology for use in treating cancer. The approach is to administer a hypoxia activated prodrug, followed by administration of another chemotherapeutic agent that is not a hypoxia activated prodrug. The median survival in pancreatic cancer patients can be extended by several months using such medicines and technology. In one embodiment, the various aspects of the invention can be put into practice using gemcitabine or other nucleoside analogs with chemotherapeutic activity. In one important aspect, the present invention provides methods of treating pancreatic cancer by administering TH-302 at a dose of either 240 mg/m$^2$ or 340 mg/m$^2$ in combination with gemcitabine to a patient in need of such treatment. Pancreatic cancer is a malignant neoplasm of the pancreas with current treatment options including surgery, radiotherapy, and chemotherapy. Gemcitabine as a single agent or in combination with other treatments is the most commonly used chemotherapeutic agent in patients with advanced pancreatic cancer. It is estimated that approximately 279,000 cases of pancreatic cancer were diagnosed worldwide in 2008. Pancreatic cancer is the fourth most common cause of cancer death both in the United States and internationally. The American Cancer Society estimates that 44,030 people were diagnosed with pancreatic cancer in the United States in 2011, and approximately 37,660 people died from the disease.

In various embodiments, the enolase protein level is determined by a method comprising quantitative western blot, multiple immunoassay formats, ELISA, immunohistochemistry, histochemistry, or use of FACS analysis of tumor lysates, immunofluorescence staining, a bead-based suspension immunoassay, Luminex technology or a proximity ligation assay (PLA). In another embodiment, the enolase RNA level is determined by a method comprising microarray chips, or RT-PCR, qRT-PCR, multiplex qPCR or in-situ hybridization.

Methods to Measure or Determine Enolase Levels

Enolase levels can be measured in accordance with the methods of the invention by any means known in the art. While enolase levels can be readily expressed in ng/ml from serum samples, other measurement units are readily useable in the methods of the invention by those of skill in the art upon contemplation of this disclosure.

In one embodiment, enolase levels are determined using a bead-based suspension immunoassay, such as provided by AssayGate, Inc., Ijamsville, Md.). In one embodiment, enolase levels are determined using an enzyme linked immunosorbent assay (ELISA). In one embodiment, enolase levels are determined using Western blot analysis. In one embodiment, enolase levels are determined using solid-phase extraction and matrix-assisted laser desorption/ionization mass spectrometry. In one embodiment, enolase levels are determined using surface-enhanced laser desorption/ionization time-of-flight (SELDI-TOF) mass spectrometry. In one embodiment, enolase levels are determined using protein arrays based on multiplexing a sandwich-ELISA system with chemiluminescent or fluorescent detection of analytes whose respective capture antibodies are spotted in arrays within each well of a sample plate (e.g., a 96-well microplate).

Enolase levels from the tissue, serum or liquid sample to be analyzed may easily be detected or isolated using techniques which are well known to one of skill in the art, including but not limited to Western blot analysis. For a detailed explanation of methods for carrying out Western blot analysis, see, e.g., Sambrook and Russell (2001) "Molecular Cloning: A Laboratory Manual," Third Edition. The protein detection and isolation methods employed herein can also be such as those described in Harlow and Lane, (1999) "Using Antibodies: A Laboratory Manual." This can be accomplished, for example, by immunofluorescence techniques employing a fluorescently labeled antibody coupled with light microscopic, flow cytometric, or fluorimetric detection. The antibodies (or fragments thereof) useful in the present disclosure may, additionally, be employed histologically, as in immunofluorescence or immunoelectron microscopy, for in-situ detection of enolase levels. In-situ detection may be accomplished by removing a histological specimen from a patient, and applying thereto a labeled antibody. The antibody (or fragment) is preferably applied by overlaying the labeled antibody (or fragment) onto a biological sample. Through the use of such a procedure, it is possible to determine not only the presence of enolase levels, but also its distribution in the examined tissue. Using the present disclosure, one of ordinary skill will readily perceive that any of a wide variety of histological methods (such as staining procedures) can be modified in order to achieve such in situ detection.

The selected marker can be particularly used to establish screening tools with a higher throughput, such as Luminex xMAP technology. Luminex color-codes tiny beads, called microspheres, into 500 distinct sets. Each bead set can be coated with a reagent specific to a particular bioassay, allowing the capture and detection of specific analytes from a sample. The Luminex technology particularly combines a sandwich ELISA immobilized on microparticle beads and flow cytometry. It allows simultaneous quantitative measurement of several proteins in one single sample. Inside the Luminex analyzer, a light source excites the internal dyes that identify each microsphere particle, and also any reporter dye captured during the assay. Dual lasers are employed to detect identity of the beads (based on the spectral properties of the beads specific for each analyte) and the amount of associated Phycoerythrin (PE) fluorescence (Hoffmann et al, 2010, Toxicology 277, 49-58). Automated imaging platforms combining fluorescence microscopy with image analyses algorithms and informatics tools enable the analyses of fluorescent images from millions of cells with a high-resolution examination of the localization of cellular components, cellular macromolecular structures and the temporal dynamics of cellular functions.

Many different types of assays are known, examples of which are set forth below, including analyses by nucleotide arrays and nucleotide filters. The hybridization conditions (temperature, time, and concentrations) are adjusted according to procedures also well known in the art. It is preferred to apply chip hybridization and/or PCR for the determination of gene expression. In another preferred embodiment, the assay of the invention involves the use of a high density oligonucleotide array. In still another preferred embodiment, the analysis is performed by multiplex qPCR, more preferably low density TaqMan arrays or branched DNA assays. Other solid supports and microarrays are known and commercially available to the skilled artisan.

The measurement of levels of expression may be carried out using any techniques that are capable of measuring RNA transcripts in a biological sample. Examples of these techniques include, without being limited thereto, PCR, Northern blotting, TaqMan, Primer Extension, Differential display and nucleotide arrays, among other things.

In another embodiment, the total RNA from the patient sample is prepared by methods known to the skilled artisan such as by Trizol (Invitrogen) followed by subsequent re-purification, e.g. via Rneasy columns (Qiagen). The total RNA is used to generate a labeled target according to methods and using detectable labels well-known in the art. For instance, the RNA may be labeled with biotin to form a cRNA target for use in an assay. Next, with the extracted mRNA as a template, cDNAs are produced using a reverse transcriptase (for example, SuperScript Reverse Transcriptase; GibcoBRL) and labeled dNTP (for example, Cy3-dUTP and Cy5-dUTP; Amersham Pharmacia Biotech), and a cDNA sample that reflects the amount of genes expressed within the cells to be evaluated is prepared. This causes labeled cDNA to be included in the cDNA sample. Here, either fluorescent label or radiolabel may be used as a label. The cDNA sample prepared in this manner is applied to the below-mentioned microarray in its single stranded denatured form, and cDNAs included in the cDNA sample are hybridized with the genes immobilized on the basal plate.

According to a preferred embodiment of the invention, the Polymerase Chain Reaction or PCR is an amplification-based assay used to measure the copy number of the gene. Detailed protocols for real-time quantitative PCR are known in the art, for example, for RNA.

Methods of real-time quantitative PCR using TaqMan probes are well-known in the art. Hence, a TaqMan-based assay can be applied to quantify polynucleotides. TaqMan based assays use a fluorogenic oligonucleotide probe that contains a 5'-fluorescent dye and a 3'-quenching agent. The probe hybridizes to a PCR product, but cannot itself be extended due to a blocking agent at the 3'-end. When the PCR product is amplified in subsequent cycles, the 5'-nuclease activity of the polymerase, for example, AmpliTaq, results in the cleavage of the TaqMan probe. This cleavage separates the 5'-fluorescent dye and the 3'-quenching agent, thereby resulting in an increase in fluorescence as a function of amplification.

The analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion. Optical images viewed and optionally recorded by a camera or other recording device (e.g. a photodiode and data storage device) are optionally further processed in any of the embodiments herein, e.g. by digitizing the image, storing and/or analyzing the image on a computer. A variety of commercially available peripheral equipment and software is available for digitizing, storing and analyzing a digitized video or digitized optical image. One conventional system carries light from the specimen field to a cooled charge-coupled device (CCD) camera, in common use in the art. A CCD camera includes an array of picture elements (pixels). The light from the specimen is imaged on the CCD. Particular pixels corresponding to regions of the specimen are sampled to obtain light intensity readings for each position. Multiple pixels are processed in parallel to increase speed. The apparatus and methods of the invention are easily used for viewing any sample, e.g. by fluorescent or dark field microscopic techniques.

Further methods are disclosed in US 2009/0202989, US 2010/0221754, US 2011/0275088, US 2012/0089541, US 2013/0102493 and U.S. Ser. No. 14/375,417, each of which is incorporated herein by reference.

Thus, any of a variety of means can be used to assess enolase levels in a patient or sample taken from the patient for the purpose of predicting whether the patient will respond favorably to hypoxia-activated prodrug therapy. If the enolase level in the patient or patient sample is higher than or equal to a predetermined value for the enolase level, the patient is administered a HAP therapy, such as TH-302, but if the enolase level is below that predetermined value, then the patient is administered an anti-cancer therapy other than HAP therapy.

Example

Most solid tumors have significant areas of hypoxia that contain cells that are resistant to traditional chemotherapy and radiation treatment. Thus, therapeutics that can specifically target these resistant hypoxic zones should provide additional anti-tumor activity and clinical benefit. TH-302 is a hypoxia-targeted prodrug of a DNA alkylating agent that is being tested in multiple oncology clinical trials. More specifically, TH-302 is a nitroimidazole-linked prodrug of a brominated version of isophosphoramide mustard (Br-IPM). TH-302 is reduced at the nitroimidazole site of the prodrug by intracellular reductases, and when exposed to hypoxic conditions, leads to the release of Br-IPM. There are several factors that affect the sensitivity of different cancer models to TH-302 including the degree of hypoxia in the tumor, intracellular reductase enzymes such as NADPH:cytochrome P450 (CYPOR) and mutations in DNA repair genes such as BRCA1, BRCA2 or FANCA. The precise one-electron reductase enzymes in different cancer cell types that can mediate the activation of TH-302 under hypoxic conditions are currently not well understood.

In previous tumor xenograft studies from a variety of different tumor types, the monotherapy efficacy of TH-302 was modest since tumor growth delays were typically observed in a panel of 11 cancer cell-line derived models (Sun et al., 2012, Clin Cancer Res 18:758-770). This level of efficacy is consistent with a mechanism of action of TH-302, whereby TH-302 targets the hypoxic tumor regions that typically comprise approximately 2-25% of the entire tumor.

In the TH-CR-404 Phase II clinical trial in pancreatic cancer (NCT01144455), pancreatic cancer patients with locally advanced or metastatic disease were randomized in three study arms to receive Gemcitabine (Gem) therapy or the combination of Gemcitabine with one of 2 dose levels of TH-302. TH-302 was administered either at 240 or 340 $mg/m^2$ by intravenous infusion. A total of 214 patients were enrolled (Gemcitabine arm, n=69; Gemcitabine+TH-302 240 $mg/m^2$, n=71; Gemcitabine+TH-302 340 $mg/m^2$, n=74). This trial met its primary endpoint of improved progression free survival (PFS) in the Gemcitabine+TH-302 groups as compared to Gemcitabine alone, with PFS improvement being greatest in the high-dose TH-302 group (HR=0.58, p=0.008) (Borad et al., 2012, Cancer Res 72(8 Suppl 1): Abstract LB-121).

To search for potentially predictive serum biomarkers of the clinical benefit derived from TH-302 hypoxia-activated therapy, an initial search of candidate biomarkers was conducted from the trial pre-treatment serum samples using a multiplexed bead-based immunoassay (AssayGate, Inc., Ijamsville, Md.). When measuring serum samples for ENO1 and ENO2 protein levels by means of this bead-based, suspension immunoassay format for ENO1, the limit of detection of the assay was 1.8 ng/ml. For ENO2, the assay sensitivity was 1.2 ng/ml.

Figure 1B:
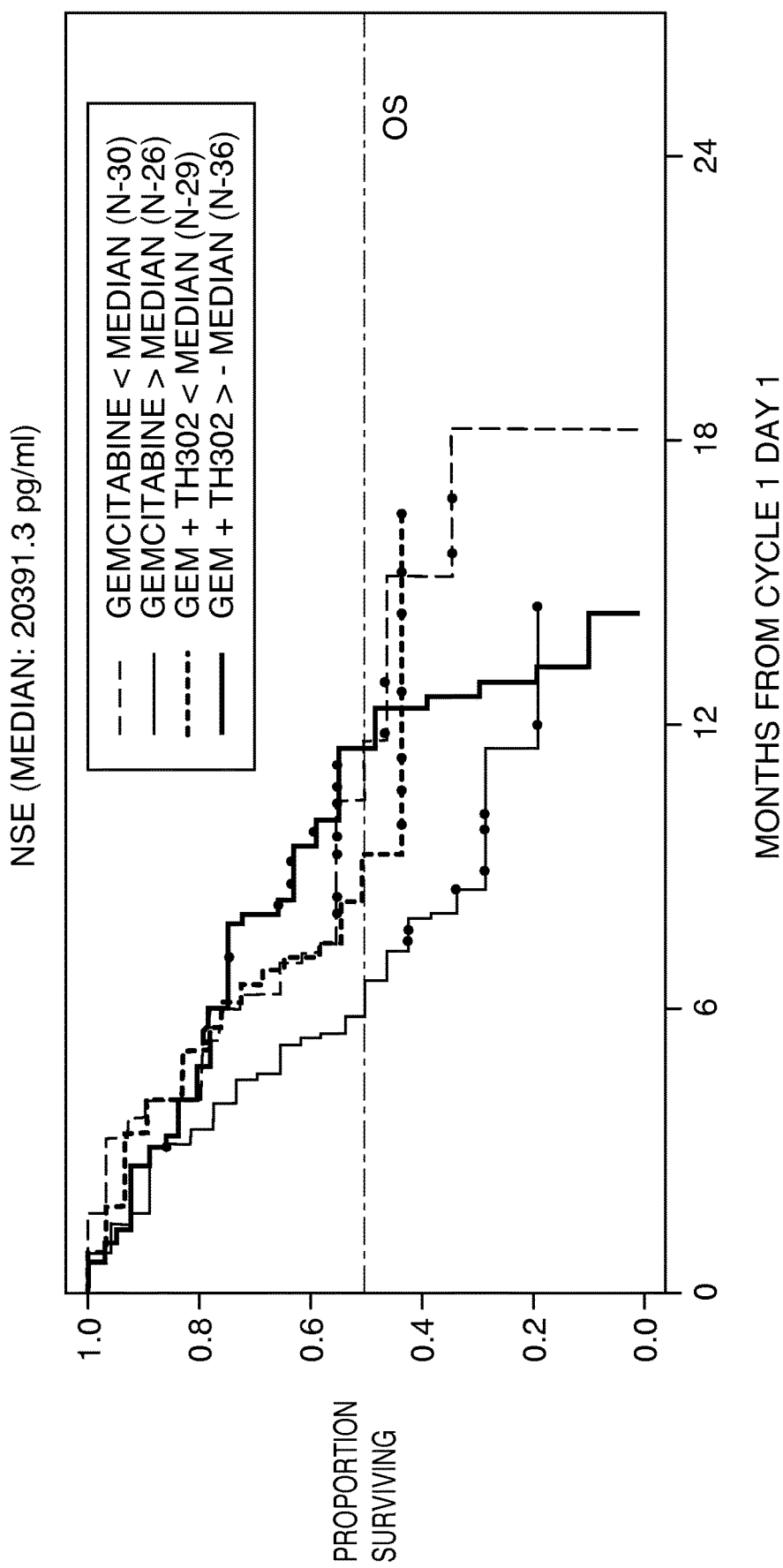
Figure 2A:
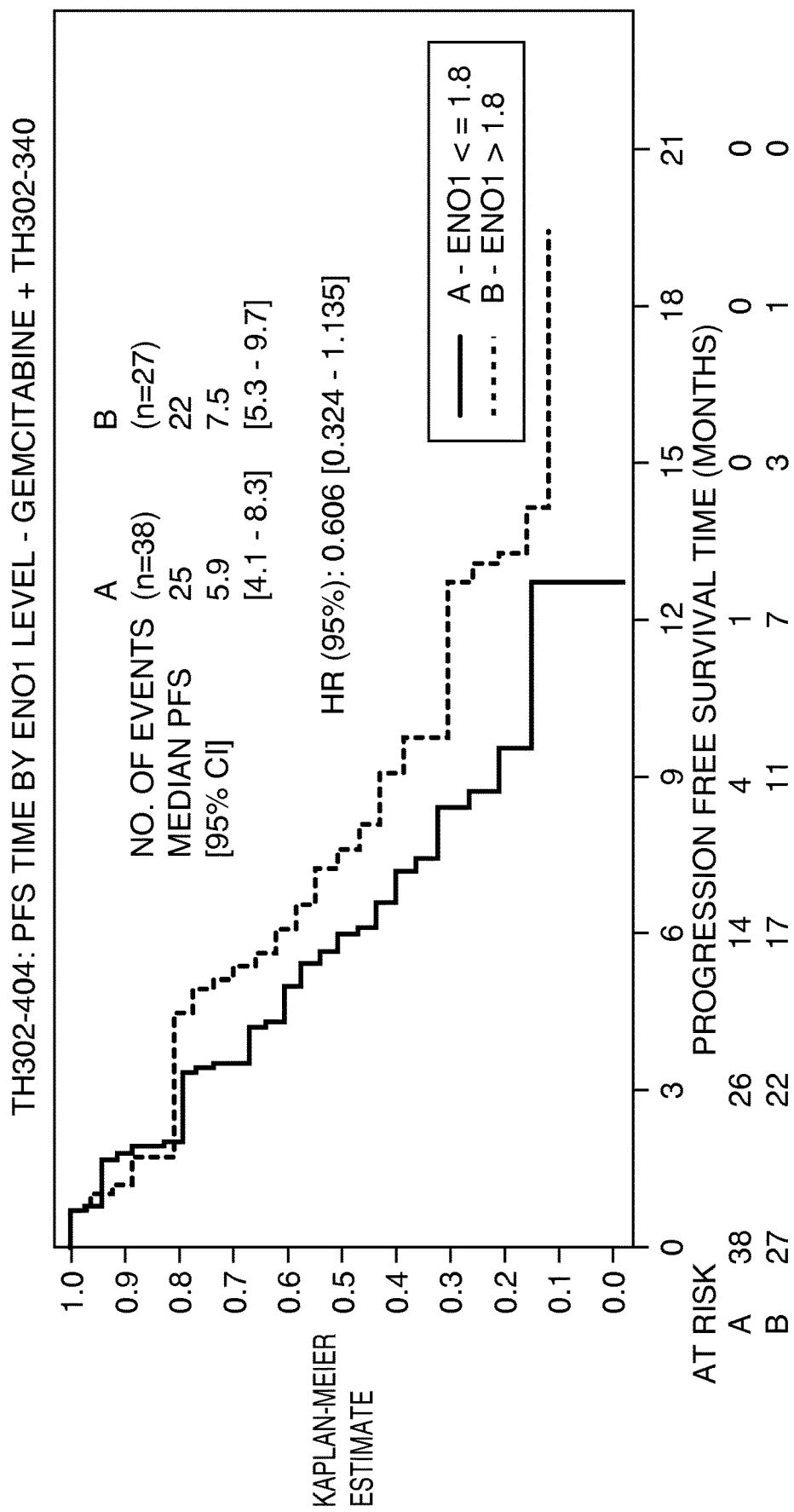
FIG. 2 shows Kaplan-Meier Progression Free Survival (PFS) (FIG. 2A) and Overall Survival (OS) (FIG. 2B) graphs for patients receiving Gem+TH-302 340 mg/m$^2$ based on detectable levels of ENO1 (enolase 1, α-enolase). Further analyses of OS comparing patients with the upper third levels of ENO1 (FIG. 2C) or upper quartile (FIG. 2D) are also shown. In detail.
Figure 2B:
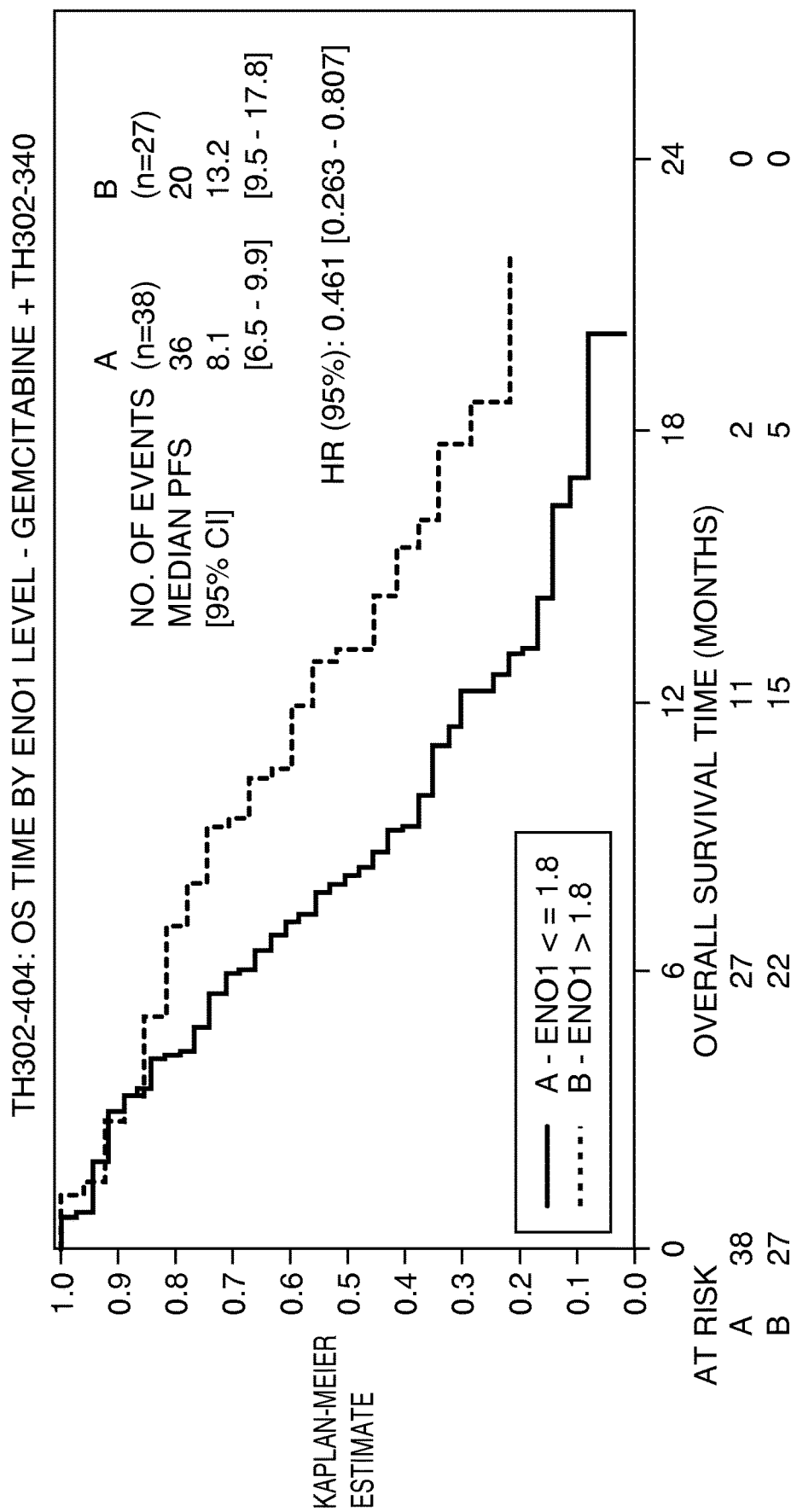
Figure 2C:
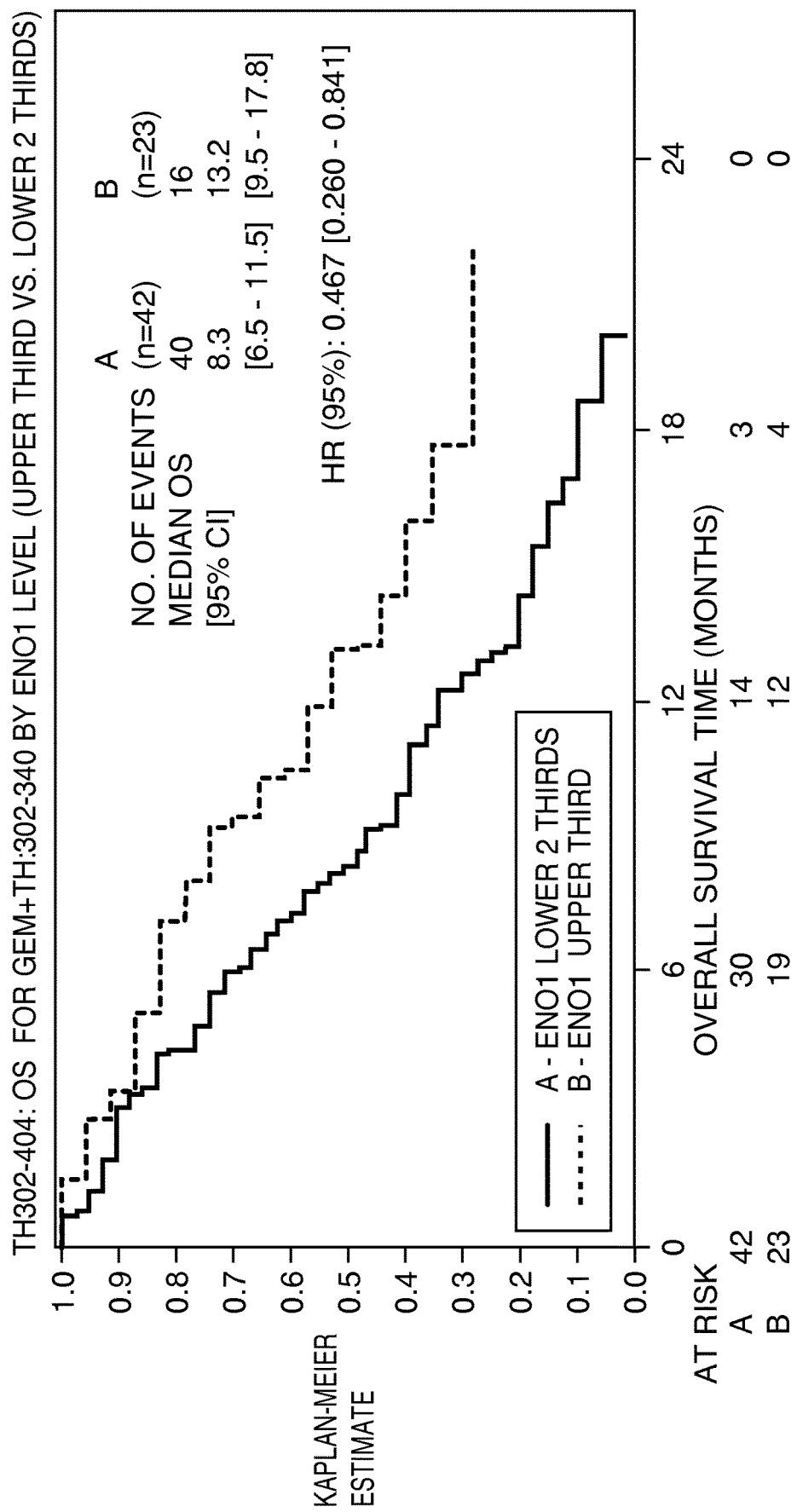
Figure 2D:
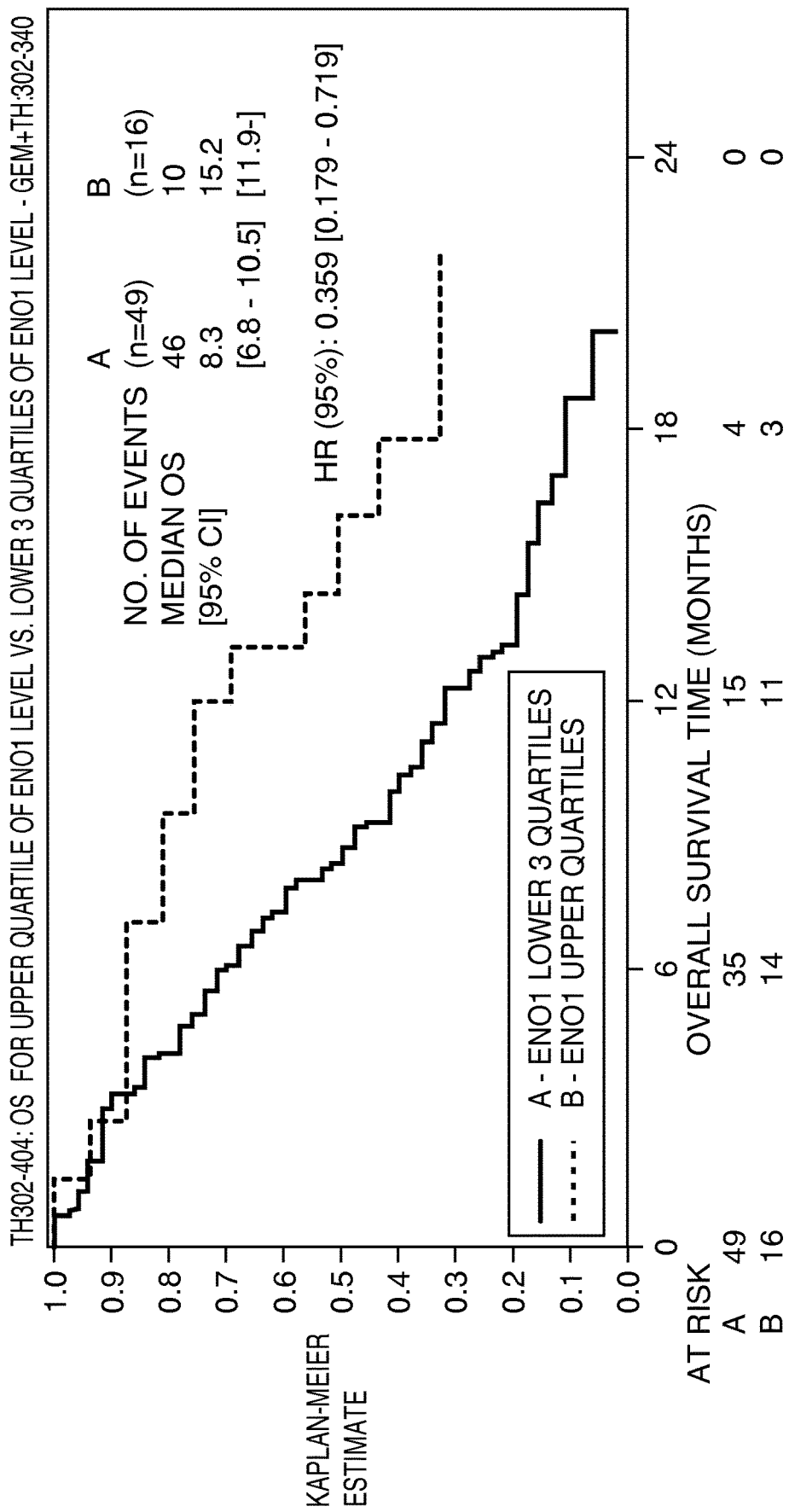

Surprisingly, ENO2 (enolase 2), also known as NSE (neural-specific enolase) was identified as a candidate biomarker based on the potential association of high levels of ENO2 with improved progression-free survival (PFS) and overall survival (OS) (FIG. 1). Differences between treatment groups of median PFS and OS times were more pronounced among patients with high ENO2. Following the identification of ENO2 as a potentially predictive biomarker for the clinical benefit derived from TH-302, the levels of ENO1 were tested in the same patient serum samples (Harris A L, 2002, Nat Rev Cancer 2: 38-47; Semenza G L, 2003, Nat Rev Cancer 3: 721-732). High levels of ENO1 were associated with improved PFS and OS in Gemcitabine+TH-302 340 $mg/m^2$ patient samples in this trial (FIG. 2). These associations were shown using the ENO1 cut-off value of the assay sensitivity limit (1.8 ng/ml) (FIGS. 2A and 2B). When the cutoff value was increased to stratify those patients based on ENO1 levels in the highest upper third or highest upper quartile, the predictive effect of ENO1 level on the overall survival of the patients was even more pronounced (FIGS. 2C and 2D). These data shown in FIG. 2 surprisingly demonstrated a promising biomarker effect for ENO1 for OS in chemotherapy naïve patients undergoing treatment with Gem+TH-302 340 $mg/m^2$.

In conclusion, these data and analyses identified enolase expression levels as a potential biomarker to predict which patients will be most likely to show a high level of response to TH-302, whether in combination therapy with gemcitabine or alone. The predictive value of enolase expression levels are related to TH-302 based on its mechanism of action as a hypoxia-activated prodrug. Both ENO1 and ENO2 were identified as biomarkers that were predictive of the clinical benefit derived from the TH-302 hypoxia-activated therapy in cancer patients.

The invention claimed is:

1. A method for treating cancer in a patient, comprising the steps of determining that an enolase RNA or protein level in a cancer sample isolated from said patient exceeds a predetermined level and administering to said patient a hypoxia-activated prodrug of formula (I)

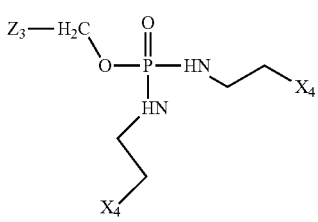

wherein $Z_3$ is selected from the group consisting of:

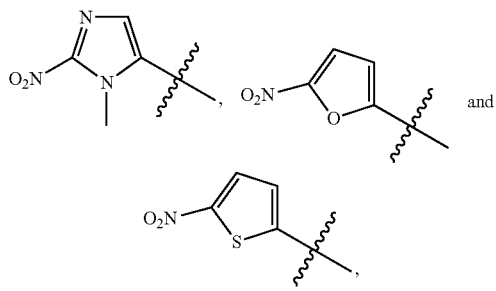

and $X_4$ is Cl or Br, or a physiologically acceptable salt thereof;
wherein the predetermined level of enolase is equal to or greater than 1.8 ng/ml; and
wherein the hypoxia-activated prodrug is administered in an amount of about 100 mg/m$^2$ to about 700 mg/m$^2$ to the patient in need of cancer therapy.

2. The method according to claim 1, wherein the hypoxia-activated prodrug comprises (2-bromoethyl)({[(2-bromoethyl)amino][(2-nitro-3-methylimidazol-4-yl)methoxy]phosphoryl})amine (TH-302) or (2-chloroethyl)({[(2-chloroethyl)amino][(2-nitro-3-methylimidazol-4-yl)methoxy]phosphoryl})amine (TH-281).

3. The method of claim 1, wherein the cancer patient is suffering from pancreatic cancer.

4. The method of claim 1, wherein the enolase is EN01 (α-enolase), EN02 (γ-enolase) and/or EN03 (β-enolase).

5. The method of claim 1, wherein the hypoxia-activated prodrug is administered intravenously in an amount of about 240 mg/m$^2$ to about 340 mg/m$^2$ to the patient in need of cancer therapy.

6. The method of claim 1, wherein the hypoxia-activated prodrug is administered in combination with an anticancer drug that is not a hypoxia-activated prodrug.

7. The method of claim 1, wherein the patient sample is one or more of a serum sample, plasma sample, whole blood sample, pancreatic juice sample, tissue sample, tumor sample or tumor lysate.

8. The method of claim 1, wherein the enolase RNA level is determined by a method comprising PCR, qRT-PCR, multiplex qPCR or in-situ hybridization, or the enolase protein level is determined by a method comprising immunohistochemistry, histochemistry, western blot, FACS, immunofluorescence staining, a bead-based suspension immunoassay, Luminex technology or a proximity ligation assay.

9. The method of claim 1, wherein the hypoxia-activated prodrug is administered in combination with gemcitabine.

* * * * *